(12) United States Patent
Kelley et al.

(10) Patent No.: US 9,315,481 B2
(45) Date of Patent: Apr. 19, 2016

(54) COMPOUNDS AND METHODS FOR TREATING LEUKEMIA

(71) Applicant: INDIANA UNIVERSITY RESEARCH AND TECHNOLOGY CORPORATION, Indianapolis, IN (US)

(72) Inventors: Mark R. Kelley, Zionsville, IN (US); Melissa L. Fishel, Indianapolis, IN (US); Angelo A. Cardoso, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 14/384,814

(22) PCT Filed: Mar. 13, 2013

(86) PCT No.: PCT/US2013/030748
§ 371 (c)(1),
(2) Date: Sep. 12, 2014

(87) PCT Pub. No.: WO2013/138430
PCT Pub. Date: Sep. 19, 2013

(65) Prior Publication Data
US 2015/0018355 A1 Jan. 15, 2015

Related U.S. Application Data

(60) Provisional application No. 61/610,722, filed on Mar. 14, 2012.

(51) Int. Cl.
| | | |
|---|---|---|
| A61K 31/535 | (2006.01) |
| C07D 295/192 | (2006.01) |
| A61K 45/06 | (2006.01) |
| A61K 31/16 | (2006.01) |
| A61K 31/164 | (2006.01) |
| A61K 31/201 | (2006.01) |
| A61K 31/381 | (2006.01) |
| A61K 31/45 | (2006.01) |
| A61K 31/475 | (2006.01) |
| A61K 31/495 | (2006.01) |
| A61K 31/519 | (2006.01) |
| A61K 31/5375 | (2006.01) |
| A61K 31/573 | (2006.01) |
| A61K 31/704 | (2006.01) |
| C07C 49/563 | (2006.01) |
| C07C 59/90 | (2006.01) |
| C07C 235/78 | (2006.01) |
| C07D 211/40 | (2006.01) |

(52) U.S. Cl.
CPC ............ *C07D 295/192* (2013.01); *A61K 31/16* (2013.01); *A61K 31/164* (2013.01); *A61K 31/201* (2013.01); *A61K 31/381* (2013.01); *A61K 31/45* (2013.01); *A61K 31/475* (2013.01); *A61K 31/495* (2013.01); *A61K 31/519* (2013.01); *A61K 31/5375* (2013.01); *A61K 31/573* (2013.01); *A61K 31/704* (2013.01); *A61K 45/06* (2013.01); *C07C 49/563* (2013.01); *C07C 59/90* (2013.01); *C07C 235/78* (2013.01); *C07D 211/40* (2013.01)

(58) Field of Classification Search
USPC ..................................................... 514/237.5
See application file for complete search history.

(56) References Cited

U.S. PATENT DOCUMENTS

| | | |
|---|---|---|
| 2004/0039061 A1 | 2/2004 | Suzuki et al. |
| 2009/0247472 A1 | 10/2009 | Depierre et al. |
| 2010/0285008 A1 | 11/2010 | Kelley |

FOREIGN PATENT DOCUMENTS

| | | |
|---|---|---|
| WO | 2012162589 A1 | 11/2012 |
| WO | 2012167122 A1 | 12/2012 |

OTHER PUBLICATIONS

J. G. Cannon, Chapter Nineteen in Burger's Medicinal Chemistry and Drug Discovery, Fifth Edition, vol. I: Principles and Practice, Wiley-Interscience 1995, pp. 783-802.*

Mathisen (Expert Opinion on Emerging Drugs (2014) 19:37-50).*

PCT International Search Report and Written Opinion completed May 1, 2013 by the ISA/US and issued in connection with PCT/US2013/030748.

Fishel M L et al., "Inhibition of the redox function of APE1/Ref-1 in myeloid leukemia cell lines results in a hypersensitive response to retinoic acid-induced differentiation and apoptosis," Experimental Hematology, Elsevier Inc., vol. 28, No. 12, Dec. 1, 2010, pp. 1178-1188.

* cited by examiner

*Primary Examiner* — Marcos Sznaidman
(74) *Attorney, Agent, or Firm* — Stinson Leonard Street LLP

(57) ABSTRACT

Compounds, and methods and uses of compounds, and pharmaceutical compositions thereof, are described herein for treating leukemia. In particular, compounds, and methods and uses of compounds, and pharmaceutical compositions thereof, are described herein for treating acute lymphoblastic leukemia (ALL) in its various forms.

5 Claims, 8 Drawing Sheets

COMPOUNDS AND METHODS FOR TREATING LEUKEMIA

CROSS-REFERENCE TO RELATED APPLICATIONS

This application is a U.S. national counterpart application of international application No. PCT/US2013/030748 filed Mar. 13, 2013, which claims priority under 35 USC §119(e) to U.S. Provisional Patent Application No. 61/610,722, filed on Mar. 14, 2012, the entire disclosures of which are hereby incorporated by reference.

TECHNICAL FIELD

The invention described herein pertains to compounds, and methods and uses of compounds and pharmaceutical compositions thereof, for treating leukemia. The invention described herein also pertains to compounds, and methods and uses of compounds and pharmaceutical compositions thereof, for treating acute lymphoblastic leukemia (ALL) in its various forms.

BACKGROUND AND SUMMARY OF THE INVENTION

Acute lymphoblastic leukemia (ALL) is the most frequent childhood cancer, with T-cell ALL representing around 15% of the cases. T-cell ALL is a lymphoproliferative disorder characterized by the deregulated expansion of transformed T-cells. Despite successes in the treatment, leukemia relapse, refractory disease, induction failure, and infant leukemia represent significant challenges in pediatric ALL and pediatric T-ALL, as well as adult disease, and these diseases remain highly untreatable. In T-cell ALL (T-ALL) in particular, disease relapse and deficient response to conventional therapies are associated with poor prognosis. Therefore, the development of novel, more effective therapies for relapsed ALL is necessary.

Prior attempts have been made to develop approaches that can successfully disrupt or abrogate critical molecular effectors in leukemia relapse, refractory T-cell leukemia, and progress in the molecular characterization of T-ALL raised expectations of the development of more selective and efficient targeted therapies. Nonetheless, despite such progress, interventions targeting key oncogenic drivers, such as Notch signaling, or single molecular effectors showed limited efficacy. The challenge remains to identify master molecular regulators that control the activity of multiple complementary, non-recurrent signaling pathways in leukemia cells, integrating oncogenic signals and microenvironment cues.

An alternative to using multiple drugs to disrupt distinct molecular pathways is to target a central molecule whose function regulates multiple signaling cascades, such as the activity of distinct transcription factors (TFs) engaged by upstream signals (oncogenic events, cytokines). The compounds, compositions, and methods described herein target multiple signaling pathways that mediate or regulate key functions in drug resistance and maintenance of tumor cells, particularly in advanced disease and cancer recurrence.

It has been discovered herein that selective inhibition of the redox function of Ref-1 is useful in treating leukemia, including ALL in its various forms. The role of Ref-1 in leukemia drug-resistance and ALL relapse has heretofore been unknown. It has been discovered herein that leukemia cells, including human leukemia T-ALL cells, express Ref-1.

Without being bound by theory, it is believed herein that ALL is treatable by selectively inhibiting the redox function of Ref-1. Described herein are compounds and methods for inhibiting the redox function of Ref-1. Without being bound by theory, it is also believed herein that ALL is treatable by interfering with STAT3 signaling. Described herein are methods for directly interfering with STAT3 signaling, and indirectly interfering with STAT3 signaling.

In one illustrative embodiment of the invention, there is provided a method for treating leukemia in a patient in need thereof comprising the step of administering an effective amount of at least one Ref-1 redox inhibitor of the formula

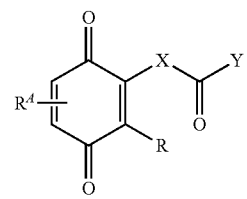

or a pharmaceutically acceptable salt thereof, wherein R, $R^4$, X and Y are defined below.

In addition, various genera and subgenera of each of R, $R^4$, X and Y are described herein. It is to be understood that all possible combinations of the various genera and subgenera of each of R, $R^4$, X and Y described herein represent additional illustrative embodiments of compounds of the invention described herein. It is to be further understood that each of those additional illustrative embodiments of compounds may be used in any of the compositions, methods, and/or uses described herein.

In another embodiment, pharmaceutical compositions containing one or more of the compounds are also described herein. In one aspect, the compositions include a therapeutically effective amount of the one or more compounds for treating a patient with a leukemia as disclosed herein. It is to be understood that the compositions may include other component and/or ingredients, including, but not limited to, other therapeutically active compounds, and/or one or more carriers, diluents, excipients, and the like. In another embodiment, methods for using the compounds and pharmaceutical compositions for treating patients with a leukemia as disclosed herein are also described herein. In one aspect, the methods include the step of administering one or more of the compounds and/or compositions described herein to a patient with a leukemia as disclosed herein. In another aspect, the methods include administering a therapeutically effective amount of the one or more compounds and/or compositions described herein for treating patients with a leukemia as disclosed herein. In another embodiment, uses of the compounds and compositions in the manufacture of a medicament for treating patients with a leukemia as disclosed herein are also described herein. In one aspect, the medicaments include a therapeutically effective amount of the one or more compounds and/or compositions for treating a patient with a leukemia as disclosed herein.

It is appreciated herein that the compounds described herein may be used alone or in combination with other compounds useful for treating a leukemia as disclosed herein, including those compounds that may be therapeutically effective by the same or different modes of action. In addition, it is appreciated herein that the compounds described herein may

BRIEF DESCRIPTION OF THE DRAWINGS

FIG. 2B shows the efficacy of Examples 5a, 5c, and 5e against T-ALL primary cells from three patients $P_3$, $P_R$, and $P_B$, as a function of concentration (μM).

DETAILED DESCRIPTION

Figure 1:
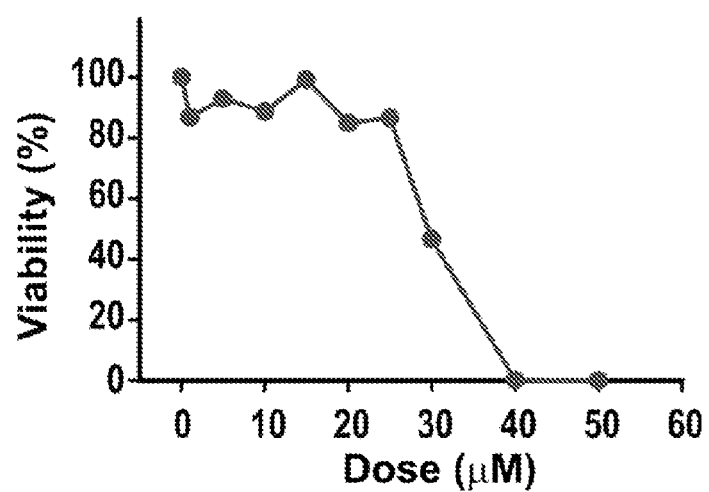
FIG. 1 shows the dose response viability of TAIL7 cells derived from relapsed ALL patient treated with E3330.

In one embodiment, there is provided a method of treating leukemia in a patient in need thereof comprising the step of administering an effective amount of at least one Ref-1 redox inhibitor of the formula

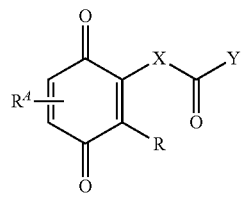

or a pharmaceutically acceptable salt thereof, wherein:
$R^A$ represents two substituents each selected from hydrogen and alkoxy, where $R^A$ are not both hydrogen; or
$R^A$ represents a fused aryl ring that is optionally substituted;
R is hydrogen or halo, or alkyl, heteroalkyl, cycloalkyl, or cycloheteroalkyl each of which is optionally substituted;
X is alkylene, alkenylene, or alkynylene, each of which is optionally substituted; and
Y forms a carboxylic acid, ester, or amide.

In one embodiment of the above, each $R^A$ is alkoxy. In a further embodiment, each $R^A$ is methoxy.

In another embodiment of the above, $R^A$ represents optionally substituted benzo. In a further embodiment, $R^A$ represents benzo.

In one embodiment of any the above, R is alkyl or heteroalkyl, each of which is optionally substituted. In a further embodiment, R is optionally substituted alkyl. In yet a further embodiment, R is alkyl.

In another embodiment of any of the above, R is alkoxy. In a further embodiment, R is methoxy.

In another embodiment of any of the above, R is alkylthio.

In one embodiment of any of the above, X is optionally substituted alkylene.

In another embodiment of any of the above, X is an epoxy alkylene.

In another embodiment of any of the above, X is optionally substituted alkenylene.

In another embodiment of any of the above, X is alkyl substituted alkenylene. In a further embodiment, X is 2-alkylethylene.

In one embodiment of any of the above, Y is OH.

In another embodiment of any of the above, Y forms an ester.

In another embodiment of any of the above, Y forms an amide.

In one embodiment, Y is $N(R^1)_2$ where each $R^1$ is independently selected from the group consisting of hydrogen, alkyl, heteroalkyl, cycloalkyl, and cycloheteroalkyl, each of which is optionally substituted, or both $R^1$ are taken together with the attached nitrogen to form an optionally substituted heterocycle. In one embodiment, at least one $R^1$ is hydroxyalkyl. In another embodiment, at least one $R^1$ is polyhydroxyalkyl. In another embodiment, each $R^1$ is optionally substituted alkyl. In another embodiment, each $R^1$ is alkyl. In another embodiment, both $R^1$ are taken together with the attached nitrogen to form an optionally substituted heterocycle selected from the group consisting of pyrrolidine, piperidine, piperazine, and morpholine.

In another embodiment, Y is $NR^2OR^2$, where each $R^2$ is independently selected from the group consisting of hydrogen, alkyl heteroalkyl, cycloalkyl, and cycloheteroalkyl, each of which is optionally substituted, and a prodrug group, or both $R^2$ are taken together with the attached nitrogen and oxygen to form an optionally substituted heterocycle. In one embodiment, at least one $R^2$ is hydrogen. In another embodiment, at least one $R^2$ is optionally substituted alkyl. In a further embodiment, at least one $R^2$ is alkyl. In another embodiment, both $R^2$ are taken together with the attached nitrogen and oxygen to form an optionally substituted heterocycle selected from the group consisting of oxazolidine, oxazine, and oxazapine.

In one embodiment of any of the above, at least one Ref-1 redox inhibitor is E3330 (also known as APX3330).

In another embodiment of any of the above, at least one Ref-1 redox inhibitor is other than E3330.

Another embodiment of any of the above is the method comprising further administering an antileukemia chemotherapeutic agent or an antileukemia enzyme inhibitor.

In one embodiment of any of the above, the leukemia is acute lymphoblastic leukemia (ALL). In another embodiment of any of the above, the leukemia is pediatric (childhood) ALL. In another embodiment of any of the above, the leukemia is infant ALL. In another embodiment of any of the above, the leukemia is T-cell ALL (T-ALL). In another embodiment of any of the above, the leukemia is relapsed ALL. In another embodiment of any of the above, the leukemia is refractory ALL. In another embodiment of any of the above, the leukemia is drug-resistant ALL. In a further embodiment, the leukemia is glucocorticoid-resistant ALL.

Several illustrative embodiments of the invention are described by the following enumerated clauses:

1. A method for treating leukemia in a patient, the method comprising the step of administering an effective amount of at least one compound of the formula

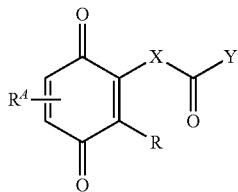

or a pharmaceutically acceptable salt thereof, wherein:

$R^A$ represents two substituents each selected from hydrogen and alkoxy, where $R^A$ are not both hydrogen; or $R^A$ represents a fused aryl ring that is optionally substituted;

R is hydrogen or halo, or alkyl, heteroalkyl, cycloalkyl, or cycloheteroalkyl each of which is optionally substituted;

X is alkylene, alkenylene, or alkynylene, each of which is optionally substituted; and Y forms a carboxylic acid, ester, or amide.

2. Use of one or more compounds in the manufacture of a medicament for treating leukemia, wherein at least one compound is of the formula

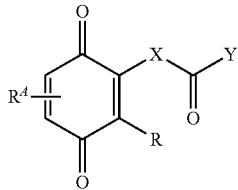

or a pharmaceutically acceptable salt thereof, wherein:

$R^A$ represents two substituents each selected from hydrogen and alkoxy, where $R^A$ are not both hydrogen; or $R^A$ represents a fused aryl ring that is optionally substituted;

R is hydrogen or halo, or alkyl, heteroalkyl, cycloalkyl, or cycloheteroalkyl each of which is optionally substituted;

X is alkylene, alkenylene, or alkynylene, each of which is optionally substituted; and Y forms a carboxylic acid, ester, or amide.

3. A composition for treating leukemia, the composition comprising at least one compound of the formula

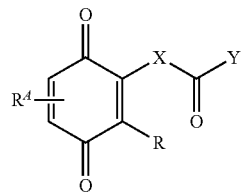

or a pharmaceutically acceptable salt thereof, wherein:

$R^A$ represents two substituents each selected from hydrogen and alkoxy, where $R^A$ are not both hydrogen; or $R^A$ represents a fused aryl ring that is optionally substituted;

R is hydrogen or halo, or alkyl, heteroalkyl, cycloalkyl, or cycloheteroalkyl each of which is optionally substituted;

X is alkylene, alkenylene, or alkynylene, each of which is optionally substituted; and Y forms a carboxylic acid, ester, or amide.

4. The method, use, or composition of any one of clauses 1-3 wherein the composition further comprises one or more carriers, diluents, or excipients, or a combination thereof.

5. The method, use, or composition of any one of clauses 1-4 wherein the compound is a selective inhibitor of the Ref-1 redox function.

6. The method, use, or composition of any one of clauses 1-5 wherein each $R^A$ is alkoxy.

7. The method, use, or composition of any one of clauses 1-5 wherein each $R^A$ is methoxy.

8. The method, use, or composition of any one of clauses 1-5 wherein $R^A$ represents optionally substituted benzo.

9. The method, use, or composition of any one of clauses 1-5 wherein $R^A$ represents benzo.

10. The method, use, or composition of any one of clauses 1-9 wherein R is alkyl or heteroalkyl, each of which is optionally substituted.

11. The method, use, or composition of any one of clauses 1-9 wherein R is optionally substituted alkyl.

12. The method, use, or composition of any one of clauses 1-9 wherein R is alkyl.

13. The method, use, or composition of any one of clauses 1-9 wherein R is alkoxy.

14. The method, use, or composition of any one of clauses 1-9 wherein R is methoxy.

15. The method, use, or composition of any one of clauses 1-9 wherein R is alkylthio.

16. The method, use, or composition of any one of clauses 1-15 wherein X is optionally substituted alkylene.

17. The method, use, or composition of any one of clauses 1-15 wherein X is an epoxy alkylene.

18. The method, use, or composition of any one of clauses 1-15 wherein X is optionally substituted alkenylene.

19. The method, use, or composition of any one of clauses 1-15 wherein X is alkyl substituted alkenylene.

20. The method, use, or composition of any one of clauses 1-15 wherein X is 2-alkylethylene.

21. The method, use, or composition of any one of clauses 1-20 wherein Y is OH.

22. The method, use, or composition of any one of clauses 1-20 wherein Y forms an ester.

23. The method, use, or composition of any one of clauses 1-20 wherein Y forms an amide.

24. The method, use, or composition of any one of clauses 1-20 wherein Y is $N(R^1)_2$ where each $R^1$ is independently selected from the group consisting of hydrogen, alkyl, heteroalkyl, cycloalkyl, and cycloheteroalkyl, each of which is optionally substituted, or both $R^1$ are taken together with the attached nitrogen to form an optionally substituted heterocycle.

25. The method, use, or composition of clause 24 wherein at least one $R^1$ is hydroxyalkyl.

26. The method, use, or composition of clause 24 wherein at least one $R^1$ is polyhydroxyalkyl.

27. The method, use, or composition of clause 24 wherein each $R^1$ is optionally substituted alkyl.

28. The method, use, or composition of clause 24 wherein each $R^1$ is alkyl.

29. The method, use, or composition of clause 24 wherein both $R^1$ are taken together with the attached nitrogen to form an optionally substituted heterocycle selected from the group consisting of pyrrolidine, piperidine, piperazine, and morpholine.

30. The method, use, or composition of any one of clauses 1-20 wherein Y is $NR^2OR^2$, where each $R^2$ is independently selected from the group consisting of hydrogen, alkyl heteroalkyl, cycloalkyl, and cycloheteroalkyl, each of which is optionally substituted, and a prodrug group, or both $R^2$ are taken together with the attached nitrogen and oxygen to form an optionally substituted heterocycle.

31. The method, use, or composition of clause 30 wherein at least one $R^2$ is hydrogen.

32. The method, use, or composition of clause 30 wherein at least one $R^2$ is optionally substituted alkyl.

33. The method, use, or composition of clause 30 wherein at least one $R^2$ is alkyl.

34. The method, use, or composition of clause 30 wherein both $R^2$ are taken together with the attached nitrogen and oxygen to form an optionally substituted heterocycle selected from the group consisting of oxazolidine, oxazine, and oxazapine.

35. The method, use, or composition of any one of clauses 1-34 wherein at least one compound is E3330.

36. The method, use, or composition of any one of clauses 1-34 wherein at least one compound is other than E3330.

37. The method of any one of the preceding clauses further comprising administering one or more antileukemia chemotherapeutic agent or one or more antileukemia enzyme inhibitor, or a combination thereof.

38. The use of any one of the preceding clauses wherein the medicament further comprises one or more antileukemia chemotherapeutic agent or one or more antileukemia enzyme inhibitor, or a combination thereof.

39. The composition of any one of the preceding clauses further comprising one or more antileukemia chemotherapeutic agent or one or more antileukemia enzyme inhibitor, or a combination thereof.

40. The method, use, or composition of any one of the preceding clauses wherein the leukemia is acute lymphoblastic leukemia (ALL).

41. The method, use, or composition of clause 40 wherein the leukemia is childhood ALL.

42. The method, use, or composition of clause 40 wherein the leukemia is infant ALL.

43. The method, use, or composition of clause 40 wherein the leukemia is T-cell ALL (T-ALL).

44. The method, use, or composition of clause 40 wherein the leukemia is relapsed ALL.

45. The method, use, or composition of clause 40 wherein the leukemia is refractory ALL.

46. The method, use, or composition of clause 40 wherein the leukemia is drug-resistant ALL.

47. The method, use, or composition of clause 40 wherein the leukemia is glucocorticoid-resistant ALL.

In each of the foregoing and following embodiments, it is to be understood that the formulae include and represent not only all pharmaceutically acceptable salts of the compounds, but also include any and all hydrates and/or solvates of the compound formulae. It is appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non crystalline and/or amorphous forms of the compounds.

It is to be understood that each of the foregoing embodiments may be combined in chemically relevant ways to generate subsets of the embodiments described herein. Accordingly, it is to be further understood that all such subsets are also illustrative embodiments of the invention described herein.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may be include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

Alkylene denotes and alkanediyl group, such as methylene, ethylene or trimethylene. Alkenylene denotes an alkenediyl group in which the bonds are not on the same carbon, for example ethenylene (1,2-ethenediyl). Alkynylene denotes an alkynediyl group, for example ethynylene.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylic acid and derivatives thereof" includes the group $CO_2H$ and salts thereof, and esters and amides thereof, and CN.

As used herein, the term "sulfinic acid or a derivative thereof" includes $SO_2H$ and salts thereof, and esters and amides thereof.

As used herein, the term "sulfonic acid or a derivative thereof" includes $SO_3H$ and salts thereof, and esters and amides thereof.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

As used herein, the term "phosphinic acid or a derivative thereof" includes $P(R)O_2H$ and salts thereof, and esters and amides thereof, where R is alkyl, alkenyl, alkynyl, cycloalkyl, cycloalkenyl, heteroalkyl, heteroalkenyl, cycloheteroalkyl, cycloheteroalkenyl, aryl, heteroaryl, arylalkyl, or heteroarylalkyl, each of which is optionally substituted.

As used herein, the term "phosphonic acid or a derivative thereof" includes $PO_3H_2$ and salts thereof, and esters and amides thereof.

As used herein, the term "hydroxylamino and derivatives thereof" includes NHOH, and alkyloxylNH alkenyloxylNH alkynyloxylNH heteroalkyloxylNH heteroalkenyloxylNH heteroalkynyloxylNH cycloalkyloxylNH cycloalkenyloxylNH cycloheteroalkyloxylNH cycloheteroalkenyloxylNH aryloxylNH arylalkyloxylNH arylalkenyloxylNH arylalkynyloxylNH heteroaryloxylNH heteroarylalkyloxylNH heteroarylalkenyloxylNH heteroarylalkynyloxylNH acyloxy, and the like, each of which is optionally substituted.

As used herein, the term "hydrazino and derivatives thereof" includes alkylNHNH, alkenylNHNH, alkynylNHNH, heteroalkylNHNH, heteroalkenylNHNH, heteroalkynylNHNH, cycloalkylNHNH, cycloalkenylNHNH, cycloheteroalkylNHNH, cycloheteroalkenylNHNH, arylNHNH, arylalkylNHNH, arylalkenylNHNH, arylalkynylNHNH, heteroarylNHNH, heteroarylalkylNHNH, heteroarylalkenylNHNH, heteroarylalkynylNHNH, acylNHNH, and the like, each of which is optionally substituted.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, $(C_1$-$C_6$ alkyl)$(C_1$-$C_6$ alkyl)amino, alkylcarbonylamino, N—$(C_1$-$C_6$ alkyl)alkylcarbonylamino, aminoalkyl, $C_1$-$C_6$ alkylaminoalkyl, $(C_1$-$C_6$ alkyl)$(C_1$-$C_6$ alkyl)aminoalkyl, alkylcarbonylaminoalkyl, N—$(C_1$-$C_6$ alkyl)alkylcarbonylaminoalkyl, cyano, and nitro; or $Z^X$ is selected from $—CO_2R^4$ and $—CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is to be understood that the foregoing publications, and each additional publication cited herein are incorporated herein by reference. It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl) pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3$-$C_{20})$alkanoyl; halo$(C_3$-$C_{20})$alkanoyl; $(C_3$-$C_{20})$alkenoyl; $(C_4$-$C_7)$cycloalkanoyl; $(C_3$-$C_6)$-cycloalkyl $(C_2$-$C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1$-$C_3)$alkyl and $(C_1$-$C_3)$alkoxy, each of which is optionally further substituted with one or more of 1 to 3 halogen atoms; optionally substituted aryl$(C_2$-$C_{16})$alkanoyl and optionally substituted heteroaryl$(C_2$-$C_{16})$ alkanoyl, such as the aryl or heteroaryl radical being unsubstituted or substituted by 1 to 3 substituents selected from the group consisting of halogen, $(C_1$-$C_3)$alkyl and $(C_1$-$C_3)$ alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1$-$C_3)$alkyl, and $(C_1$-$C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustrative routes of oral administration include tablets, capsules, elixirs, syrups, and the like.

Illustrative routes for parenteral administration include intravenous, intraarterial, intraperitoneal, epidurial, intraurethral, intrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

Depending upon the disease as described herein, the route of administration and the route by which the compounds and/or compositions are administered, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol. When given systemically, such as parenterally, illustrative doses include those in the range from about 0.01 mg/kg to about 100 mg/kg, or about 0.01 mg/kg to about 10 mg/kg, or about 0.1 mg/kg to about 100 mg/kg, or about 0.1 mg/kg to about 10 mg/kg. When given systemically, such as orally, illustrative doses include those in the range from about 0.1 mg/kg to about 1000 mg/kg, or about 0.1 mg/kg to about 100 mg/kg, or about 0.1 mg/kg to about 10 mg/kg, or about 1 mg/kg to about 1000 mg/kg, or about 1 mg/kg to about 100 mg/kg, or about 1 mg/kg to about 10 mg/kg.

In addition to the foregoing illustrative dosages and dosing protocols, it is to be understood that an effective amount of any one or a mixture of the compounds described herein can be readily determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

Illustratively, compounds described herein may be prepared as shown in the following scheme:

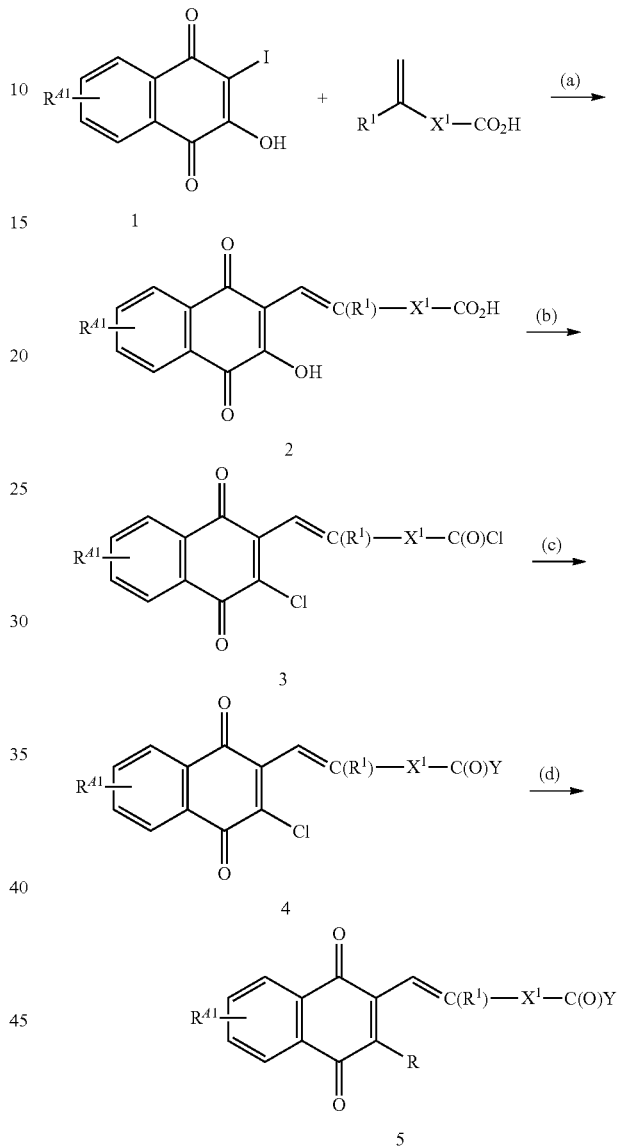

(a) 1. Pd(II)OAc, base, H$_2$O; 2. acid; (b) (COCl)$_2$, DMF, CH$_2$Cl$_2$; (c) Y—H, optional base; (d) R—H, optional base. Compounds (1) are prepared according to Perez et al., Tetrahedron Lett. 48:3995-98 (2007). In the foregoing scheme, Y and R are as defined herein, and R$^{A1}$ represents 1 to 4 optional aryl substituents; and the divalent radical CH=C(R$^1$)—X$^1$ is an embodiment of the group X, as defined herein. Additional compounds described herein are prepared by adapting the processes described in PCT/US2008/077213, the disclosure of which is incorporated herein by reference.

The human body possesses general reduction-oxidation systems (thioredoxin and glutaredoxin/glutathione) that help maintain intracellular homeostasis by scavenging reactive oxygen species (ROS). Ref-1 is nonetheless distinct and functions differently from those systems. Ref-1 does not globally reduce transcription factors; rather, it selectively influences TFs that directly govern critical cellular functions, including DNA repair, stress responses. Ref-1 also regulates other particularly critical cellular functions downstream of its effectors, including cell survival and cycle.

It has been heretofore unknown that Ref-1 plays an important, and perhaps critical, regulatory role in the biology of T-cell leukemia. It is surprisingly found that targeting Ref-1 redox activity is an effective strategy to disrupt multiple pro-survival transcription programs in drug-resistant, refractory leukemia cells. Increased Ref-1 expression has been surprisingly found to be associated with pediatric ALL (and pediatric cancers, in general). It has been discovered herein that the redox function of Ref-1 plays an important role in the proliferation and survival of T-cell ALL, including in patients' cells and in relapsed leukemia cells. Importantly, since Ref-1 regulates the activity of various transcription factors, including the leukemia-associated NF-κB, STAT3 and AP-1, its selective inactivation has the potential to disrupt multiple complementary, non-recurrent signaling pathways mediating critical processes for relapse, refractory leukemia cells. Therefore, the compounds, compositions, and, methods described herein have the potential for increased anti-tumor efficacy while reducing "therapeutic escape", where the selection of tumor variants dependent on alternative survival pathways. More broadly, the selective targeting of a key mediator of redox-regulating transcription programs in childhood leukemias represents a new therapeutic approach for relapse ALL.

Ref-1 is a multifunctional protein with DNA repair activity and a unique nuclear redox function which regulates the activity of several TFs. It has been discovered herein that Ref-1 also regulates the activity of various leukemia-associated TFs, thus controlling their transcriptional programs. In particular, Ref-1 redox function regulates the transcriptional activity of the survival-regulating transcription factors NF-κB and AP-1. It has also been discovered herein that STAT3 is required for T-cell ALL, and in particular, T-cell leukemogenesis. Deletion of STAT3 impairs the development of T-cell leukemia induced by oncogenic Notch1. STAT3 blockade inhibits T-ALL survival, and triggers potent apoptosis. STAT3 DNA binding and activity has been observed herein to be regulated by the redox function of Ref-1. It has also been discovered that Ref-1 is expressed in leukemia T-cells, including cells from biopsies of leukemia patients, primary cells from patients, relapsed T-ALL cells, and leukemia cells from Notch-induced murine T-ALL. It has also been discovered that the bone marrow (BM) of T-ALL patients showed significantly higher levels of Ref-1 transcripts ($p<0.000002$) compared to BM from normal donors.

It has also been discovered herein that STAT3 transcriptional activity is controlled at least in part by Ref-1. Without being bound by theory, it is believed herein that the compounds are efficacious against leukemia, at least in part, by facilitating, promoting, initiating apoptosis of leukemia cells. Further, though without being bound by theory, it is believed herein that the compounds are efficacious against leukemia, at least in part, by downregulation, dysregulation, or otherwise interfering with pro-survival genes that are transcriptional targets of STAT3, NF-κB, such as Survivin and Bcl-xL.

It has also been discovered that selective inactivation of Ref-1 redox provides an avenue to disrupt multiple complementary signaling pathways mediating critical processes for relapsed leukemia cells. Such disruption of multiple complementary signaling pathways represents a novel therapeutic approach for this target. In solid tumors, increased Ref-1 expression has been associated with poor prognosis and drug-resistance. The role of Ref-1 in leukemia relapse has heretofore been unknown. In addition, the role of redox control of transcription, including Ref-1 mediated redox control, in leukemia drug-resistance, which may be predictive of ALL relapse, has heretofore also been unknown. Ref-1 is expressed in childhood ALL. It has also been discovered herein that leukemia cell resistance mechanisms, such as glucocorticoid resistance, is associated with increased expression of Ref-1. Studies of leukemia cells obtained from patients indicate that T-cell ALL and its molecular regulation is more complex than the exclusive result of oncogene-triggered, cell autonomous factors. Instead, the molecular regulation involves a molecular interplay between oncogenic events and microenvironment signals, that results in increased leukemia cell fitness.

The effective use of the compounds, compositions, and methods described herein for treating or ameliorating one or more effects of a leukemic disease using one or more compounds described herein may be based upon animal models, such as murine, canine, porcine, and non-human primate animal models of disease. For example, it is understood that leukemia in humans may be characterized by a loss of function, and/or the development of symptoms, each of which may be elicited in animals, such as mice, and other surrogate test animals. In particular the murine model of relapse T-cell leukemia may be used to evaluate the methods of treatment and the pharmaceutical compositions described herein to determine the therapeutically effective amounts described herein.

The following examples and procedures further illustrate specific embodiments of the invention; however, the following illustrative examples should not be interpreted in any way to limit the invention.

EXAMPLES

Example

Dexamethasone is observed herein to upregulate Ref-1 expression in T-ALL cells, and Ref-1 levels are observed herein to increase in glucocorticoid-resistant leukemia variants. Relapsed leukemia T-cells show increased expression and activation of glucocorticoid receptor (GR) and the Ref-1 promoter contains sites for GR binding. However, Dexamethasone treatment or glucocorticoid-resistance does not result in increased levels of Ref-1 transcripts. Without being bound by theory, it is believed herein that the regulation of Ref-1 expression in leukemia T-cells may involve a post-translational mechanism, which is not regulated by Notch signaling. Blockade of Ref-1 redox markedly inhibits the viability of glucocorticoid-resistant T-ALL cells; which is important because glucocorticoid-resistant leukemia T-cells reportedly show reduced sensitivity to inhibitors of other leukemia-associated signaling pathways, such as PI3K/Akt, mTOR, and to other therapeutic drugs. It has been observed herein that Ref-1 inhibition is more effective when compared to other signaling mediators implicated in T-ALL. For example, at optimal doses that block their respective target pathways, blockade of Notch, PI3K/Akt or mTOR signaling does not surpass 70% inhibition of leukemia TAIL7 cells, whereas the compounds described herein result in a blockade of 95 to 100% inhibition.

Example

Inactivation of Ref-1 redox by the compounds described herein markedly inhibits leukemia cell survival, including primary cells from ALL patients, relapsed T-ALL, and cells from a murine model of Notch-induced leukemia. The redox function selective inhibitor E3330 markedly inhibits leukemia cell survival, including primary cells from ALL patients, relapsed T-ALL, and cells from a murine model of Notch-induced leukemia. The inhibitory effects of E3330 involve significant leukemia cell apoptosis, and correlate with downregulation of survival genes regulated by the Ref-1 'targets' STAT3 and NF-κB. Ref-1 blockade did not show a significant effect on the activation of PI3K/Akt or mTOR pathways. The activity of other selective Ref-1 redox inhibitors are analyzed against leukemia cells according to conventional redox EMSA assays. See, Su, D. et al. Interactions of APE1 with a redox inhibitor: Evidence for an alternate conformation of the enzyme. *Biochemistry* 50, 82-92 (2011). Nyland et al., Design and Synthesis of Novel Quinone Inhibitors Targeted to the Redox Function of Apurinic/Apyrimidinic Endonuclease 1/Redox Enhancing Factor-1 (Ape1/Ref-1). *J Med Chem* 53, 1200-1210 (2010). Kelley et al., *Cancer Drug Discovery and Development* (ed Rebecca G. Bagley) Springer (part of Springer Science+Business Media), 2010. Luo et al., Role of the multifunctional DNA repair and redox signaling protein Ape1/Ref-1 in cancer and endothelial cells: Small molecule inhibition of Ape1's redox function. *Antioxid Redox Signal* 10, 1853-1867 (2008). Georgiadis et al., Evolution of the redox function in mammalian Apurinic/apyrimidinic *Mutation Research* 643, 54-63 (2008).

| Example | IC$_{50}$ (μM) |
|---------|----------------|
| E3330   | 25             |
| 5a      | 1              |
| 5c      | 1              |
| 5e      | 2              |

Example

The compounds described herein decrease survival of leukemia cells. The viability of TAIL7 cells, which are derived from relapsed ALL patients, treated with E3330 is determined using a standard cell survival assay (ATP assay), at 96 h. The results are shown in FIG. 1. Blockade of Ref-1 by the redox-selective inhibitors described herein significantly inhibited leukemia T-cells, in a dose-dependent manner, using DMSO as control.

| Example | IC$_{50}$ (μM) |
|---------|----------------|
| E3330   | 29.7           |
| 5a      | 5.5            |
| 5c      | 4.2            |
| 5e      | 5.5            |

Inhibition is also seen in T-ALL lines (E3330 IC$_{50}$ 20-30 μM), from a murine model of T-cell leukemia induced by oncogenic Notch, where the cancer cells in the model were from mice with terminal disease, exhibiting significant leukocytosis, splenomegaly, and other parenchymal tissue infiltration by leukemia cells.

Example

The compounds described herein caused a substantial downregulation of survival genes regulated by STAT3 and NF-κB, such as Survivin, Bcl-xL, and miR-21. E3330 causes a 2-10 fold reduction in Survivin and Bcl-xL mRNA after 24 h at doses between 25-40 μM, as shown by quantitative PCR. Without being bound by theory, these data support that the compounds described herein may induce leukemia cell apoptosis.

Example

Figure 2A:
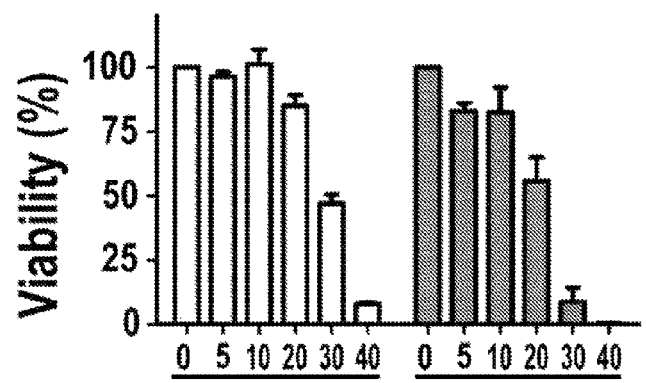
FIG. 2A shows the efficacy of E3330 against TAIL7-dexamethasone resistant cells (open bars), and TAIL7 cells (solid bars), as a function of concentration (μM).
Figure 2B:
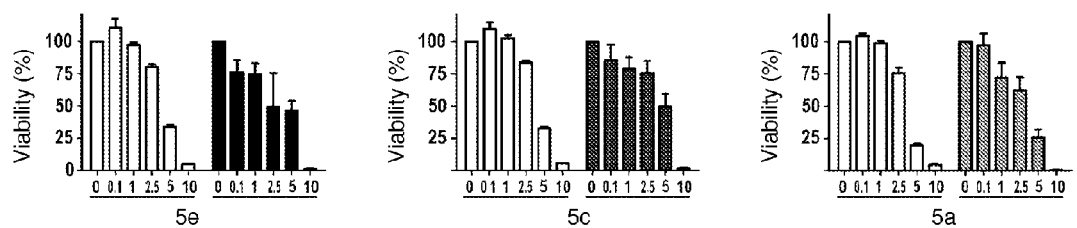
FIG. 2B shows the efficacy of Examples 5a, 5c, and 5e against TAIL7-dexamethasone resistant cells (open bars), and TAIL7 cells (solid bars), as a function of concentration (μM).

The compounds described herein are effective against resistant leukemia, including glucocorticoid-resistant ALL. Dexamethasone resistant leukemia cells are prepared by continuously culturing TAIL7 cells with 20 nM of Dexamethasone, resulting in Dexamethasone resistance (>1 μM). The compounds described herein are effective against Dexamethasone resistant leukemia cells at doses comparable to or better than needed against native TAIL7 cells using a conventional ATP assay (96 hrs, in the presence of IL-7), as shown in FIG. 2A and FIG. 2B.

Example

Figure 3A:
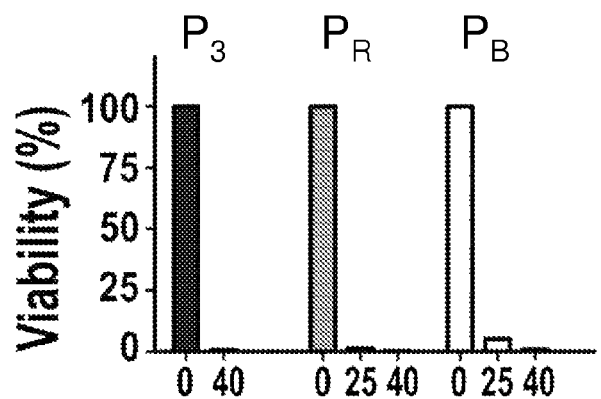
FIG. 3A shows the efficacy of E3330 against T-ALL primary cells from three patients $P_3$, $P_R$, and $P_B$, as a function of concentration (μM).
Figure 3B:
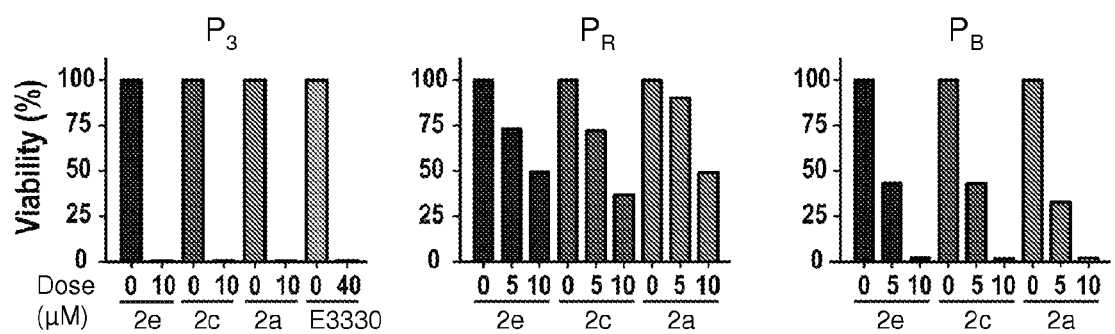

The compounds described herein are effective against primary leukemia T-ALL cells harvested from patients. The compounds described herein are effective against primary leukemia T-ALL cells harvested from patients with relapsed ALL. Cells are harvested from pediatric T-ALL patients. Patient P$_3$ is diagnosed with relapsed ALL. The results for E3330 and Examples 5a, 5c, and 5e, using a conventional ATP assay (96 hrs) against primary cells from patients P$_3$, P$_R$, and P$_B$ are shown in FIG. 3A and FIG. 3B.

Example

Figure 4:
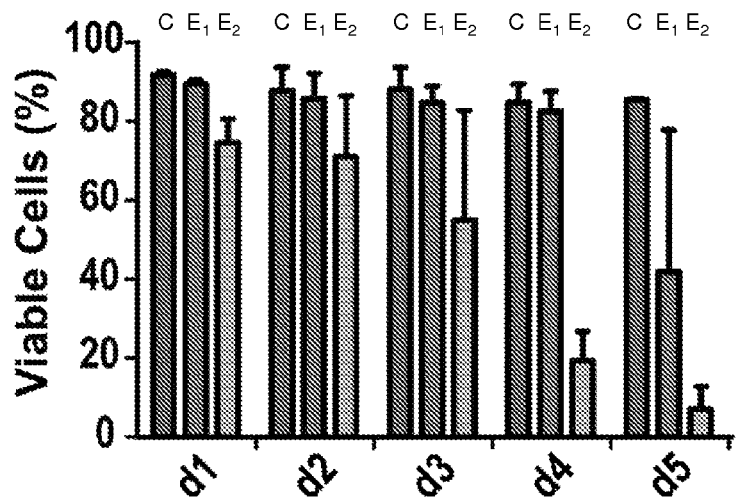
FIG. 4 shows the blockade of Ref-1 by E3330 in T-ALL cells. E3330 induces leukemia cell apoptosis, as determined in a conventional Annexin V/PI assay, over a period of five days (d1-d5), where C=vehicle control, E1=25 μM E3330, and E2=40 μM E3330.

The compounds described herein cause apoptosis of leukemia cells, including leukemia T-ALL cells. Using a conventional Annexin V/PI assay of apoptosis, T-ALL cells were treated with E3330 (25 μM or 40 μM), and compared to vehicle control over a period of five days (d1 to d5). The results are shown in FIG. 4.

Example

Figure 5:
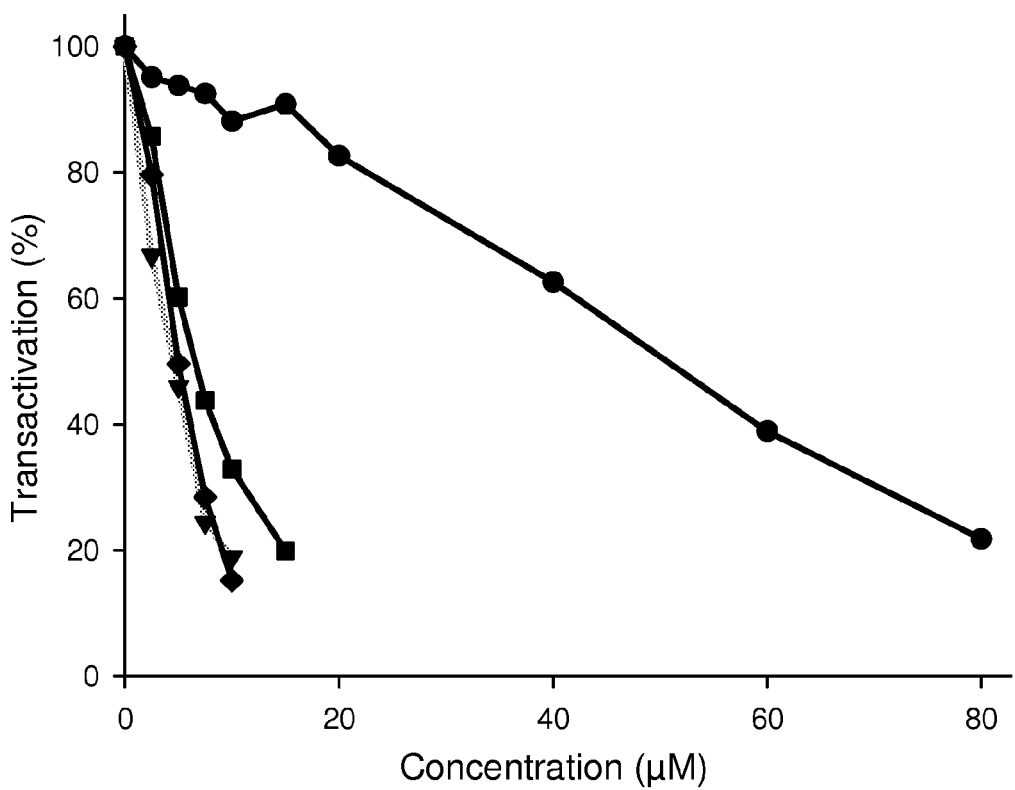
FIG. 5 shows the potency of E3330 (●), and Examples 5a (◆), 5c (■), and 5e (▼) in blocking NF κB transactivation.

The compounds described herein are effective in decreasing and/or blocking NF κB transactivation. The compounds are examined using a conventional NF κB reporter assay in cells. See, Kelley et al., Functional analysis of new and novel analogs of E3330 that block the redox signaling activity of the multifunctional AP endonuclease/redox signaling enzyme APE1/Ref-1. Antioxid Redox Signal 14, 1387-1401 (2011); Luo et al., Redox Regulation of DNA Repair: Implications for Human Health and Cancer Therapeutic Development. Antioxid Redox Signal 12, 1247-1269 (2010). The results for E3330 (●), and Examples 5a (♦), 5c (■), and 5e (▼) are shown in FIG. 5.

Example

Figure 6:
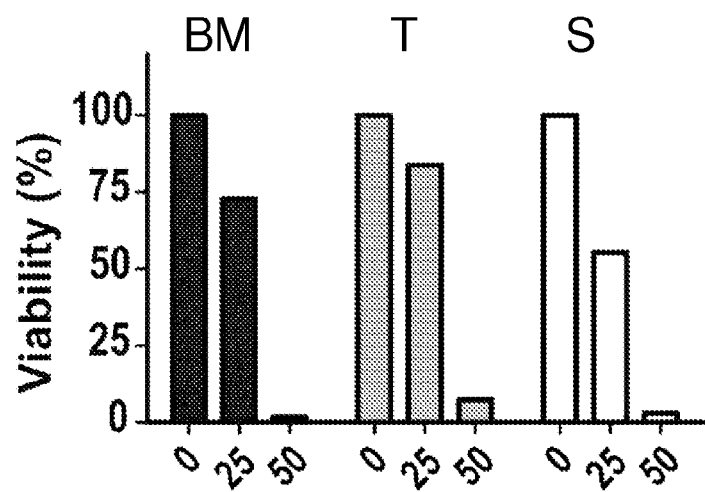
FIG. 6 shows the efficacy of E3330 against leukemia cells harvested from the bone marrow (BM), thymus (T) and spleen (S) of mice with terminal Notch (ICN)-induced T-ALL.
Figure 7A:
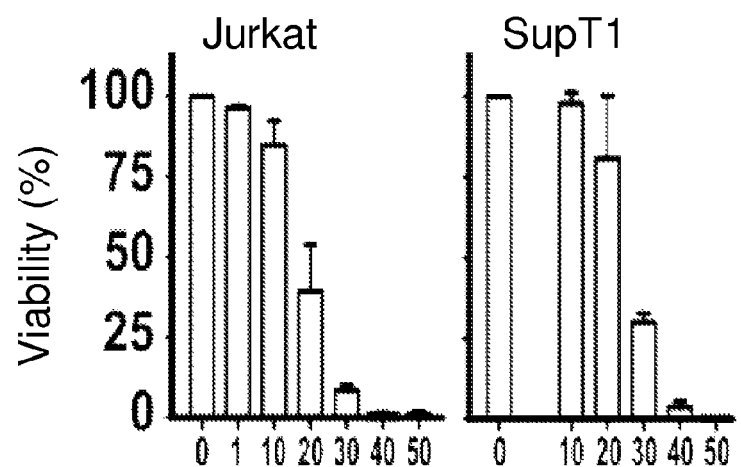
FIG. 7A shows the efficacy of E3330 against resistant Jurkat, SupT1, MOLT4, and HPB-ALL T-ALL cell lines obtained from relapse T-ALL patients, as a function of concentration (μM).
Figure 7B:
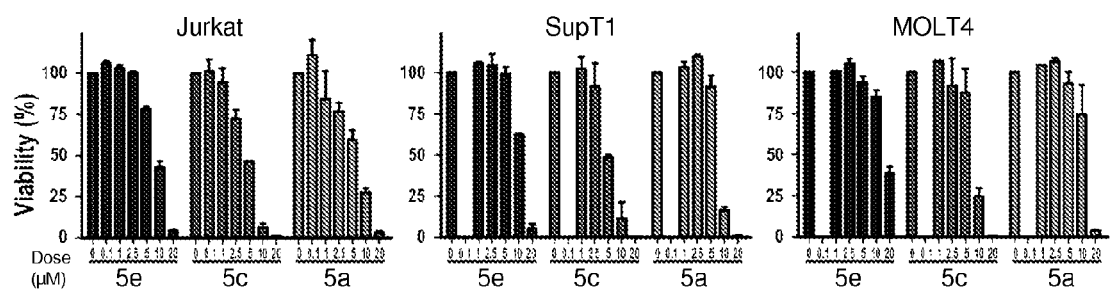
FIG. 7B shows the efficacy of Examples 5a, 5c, and 5e against resistant Jurkat, SupT1, MOLT4, and HPB-ALL T-ALL cell lines obtained from relapse T-ALL patients, as a function of concentration (μM).

The compounds described herein are effective against leukemia cells harvested from the bone marrow (BM), thymus (T) or spleen (S). Cells are harvested from the bone marrow (BM), thymus (T) or spleen (S) of mice with terminal Notch (ICN)-induced T-ALL, as determined in a conventional ATP assay (viability at 96 hrs) of the leukemia cells cultured with IL-7. The mice with terminal leukemia also exhibit high leukocytosis, splenomegaly, and CNS disease. Inhibition observed for E3330 at 25 or 50 μM is compared to vehicle control, as shown in FIG. 6. Similar inhibition is observed in immortalized Jurkat, SupT1, MOLT4, and HPB-ALL cell lines derived from relapse T-ALL patients, with IC50s from 10-30 µM. Relapse T-ALL lines (Jurkat, SupT1, MOLT4, and HPB-ALL) are reportedly resistant to treatment with glucocorticoids. The compounds described herein are also effective against TAIL7-Dexamethasone resistant cells, which show reduced sensitivity to inhibitors of other leukemia-associated signaling pathways (such as PI3K/Akt, mTOR), and to cytotoxic chemotherapy drugs. The results for E3330 and Examples 5a, 5c, and 5e are shown in FIG. 7A and FIG. 7B, respectively, as a function of concentration (µM).

Example

Figure 8A:
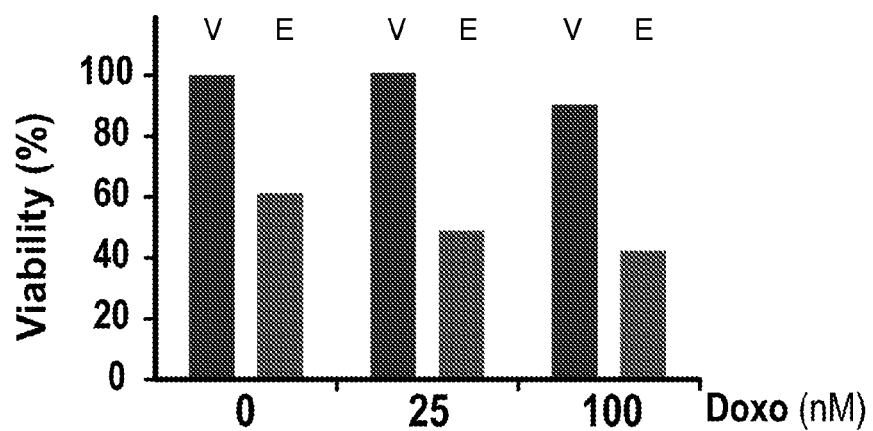
FIG. 8A shows the potentiation of doxorubicin with a fixed dose (20 μM) of E3330 (E), compared to vehicle.
Figure 8B:
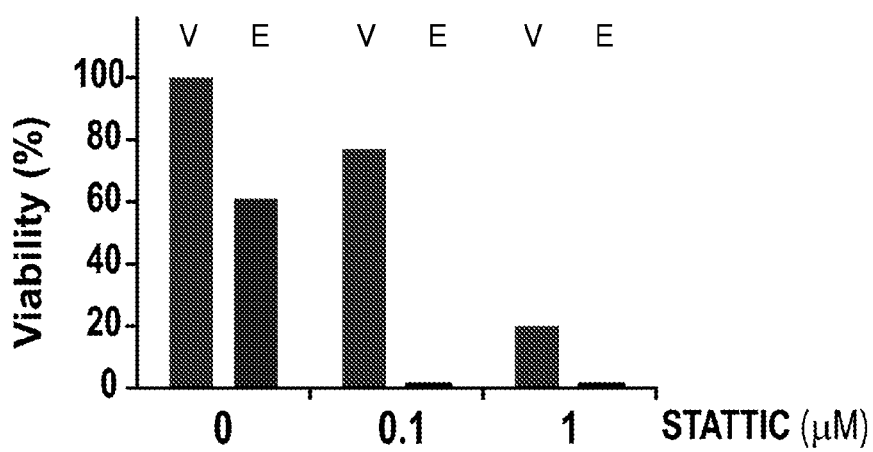
FIG. 8B shows the potentiation of STATTIC with a fixed dose (20 μM) of E3330 (E), compared to vehicle.

The compounds described herein potentiate the efficacy of conventional drugs for treating leukemia, such as doxorubicin and STATTIC. A fixed dose (20 µM) of E3330 (E) potentiates the activity of doxorubicin (Doxo) against T-ALL cells, as shown in FIG. 8A, compared to vehicle (V) in a conventional ATP assay. A fixed dose (20 µM) of E3330 (E) potentiates the activity of STATTIC against T-ALL cells, as shown in FIG. 8B, compared to vehicle (V) in a conventional ATP assay. Both doxorubicin and STATTIC are front line drugs for treating T-ALL.

Example

Murine model of relapse T-cell leukemia. The Notch-induced model of T-cell leukemia with disease relapse after Dexamethasone treatment is used. The leukemia T-cells are initially responsive to Dexamethasone. There are two therapeutic regimens: (i) relapse regimen, using compounds described herein in mice with leukemia recurrence following remission induction by Dexamethasone; and (ii) using compounds described herein plus Dexamethasone as frontline regimen, to assess the efficacy of dual therapy on preventing disease relapse.

Transplantation of Lin– hematopoietic precursor/stem cells (HPSC) transduced with ICN induces T-cell neoplasms in a dose-dependent manner. BM HPSC from C57BL/6 mice (CD45.2+) are purified, transduced with MSCV-ICN/GFP (ICN) viral particles, and sorted for GFP expression by FACS. Donor cells (20,000) are injected i.v. into lethally irradiated (10 Gy) 8-wk old recipient BoyJ mice (CD45.1+) admixed with a syngeneic radioprotective dose of $1 \times 10^5$ total BM cells. Using Lin–/HPSC as donor cells, leukemia progression correlates well with WBC counts, circulating blasts, and hepatosplenomegaly. Most cells in the leukemic mice are GFP+ and immature DP (CD4+CD8+) T-cells. Mice developing leukemia (WBC>20; >2% CD45.2+/DP cells in PB) are enrolled in studies (i), and (ii).

(i) Relapsed Leukemia Regimen. Mice developing leukemia are treated first with Dexamethasone (i.p., 15 mg/Kg, 5 d plus 2 d rest, for 2 wks) for induction of tumor remission. At evidence of leukemia relapse (>2% ALL cells in PB), mice are treated with test compound (po, 50 mg/kg/day, b.i.d, three cycles of 5 d treatment and 2 d rest), or with vehicle formulation, as control.

(ii) Relapse Prevention Regimen with test compound plus Dexamethasone. Mice developing leukemia (>2% blasts) are randomly allocated into the following treatment groups: (a) test compound plus Dexamethasone dual regimen; (b) Dexamethasone alone; (c) test compound alone; (d) control vehicles. The doses, routes, and duration of the treatments for the respective drugs are as indicated above.

Evaluation of leukemogenesis and disease progression. Animals are monitored daily, bled weekly for WBC counts and quantification of ALL cells in PB, and euthanized when moribund. Mice that do not show signs of leukemia recurrence after therapy are euthanized and analyzed at d120-d150 post-transplant (or at 10-12 wks after last therapy regimen).

PB: Emergence of the leukemia clone will be evaluated by WBC counts and increase of lymphoid cells by flow cytometry. Leukemia donor cells are confirmed, in PB and BM, by CD45.1/CD45.2, and DP staining.

BM: BM cells from femurs are analyzed for GFP, IL-7Rα/CD127, T-cell markers (CD4, CD8, CD2, CD7, CD3), and for residual normal hematopoietic stem cells (HSC; c-Kit, Sca-1 plus lineage markers). GFP+ cells are evaluated also for expression of N1 by intracellular staining. Immunoblotting (IB) and qPCR will be performed on leukemia cells (or BM from control conditions) for Notch1, Notch-IC, Hes1, Hes5, and Deltex.

Lymphohematopoietic organs: Tibias, spleen, liver, thymus, lymph nodes and abnormal masses are processed for H&E staining and histological observation. IHC is performed for T-cell markers.

CNS Disease: Reportedly, T-ALL models may evolve with CNS infiltration, which has been associated with leukemia relapse. Without being bound by theory, it is believed herein that the compounds described herein may penetrate the brain-blood barrier, and effectively target glioblastoma cells. Mice are evaluated for presence and extent of leukemia infiltration of CNS, in comparison to their respective controls.

Endpoints: (i) time of leukemia remission after therapy (relapse regimen; dual regimen); (ii) number of leukemia blasts in PB; (iii) extent of BM disease at terminal stage or at mice sacrifice (if no leukemia recurrence); (iv) extension of infiltration of parenchymal organs, including of CNS disease; (v) overall survival.

Example

Xenograft models of childhood relapse, refractory ALL. The antileukemia efficacy of Ref-1 redox blockade by the compounds described herein is evaluated in xenograft models of human ALL. In a first phase, the xenograft model with TAIL7 cells is used to test the therapeutic efficacy of the test compound as monotherapy, and in dual-agent regimens combining test compound with agents used as frontline chemotherapy for T-ALL (Vincristine; Doxorubicin; Dexamethasone) and for relapse T-ALL (Methotrexate). In a second phase, the optimal regimens (E3330 monotherapy; E3330 in dual-agent regimen) are used in xenograft models developed with leukemia cells from pediatric, relapse T-cell ALL (5 different patients). Such models of childhood ALL are used in immunodeficient mice (NOD/SCID: terminal leukemia in 70-120 d; NSG: terminal leukemia in 28-35 days with TAIL7 cells), including specimens from relapsed and infant ALL.

Xenografts of pediatric relapse T-cell leukemia: TAIL7 cells or cells from patients with relapse T-ALL (high cellularity; ≥90% BM involvement) will be used for the xenografts; patient specimens will be provided by Dr. Batra, according with IRB regulations. Leukemia cells ($1 \times 10^6$ TAIL7 cells; $2-3 \times 10^6$ patient cells/mice) will be transplanted IV into NSG mice (7-9 wk old). 19, 24 Mice will be monitored weekly for presence of human blasts in the PB, by flow cytometry. Animals exhibiting >2% circulating leukemia blasts will be randomly allocated into experimental groups, and will start treatment.

Therapeutic regimens. The following regimens will be evaluated:

(i) Test compound Monotherapy. Mice are treated with test compound (po; 50 mg/kg/day; b.i.d.) for three cycles (5 d treatment and 2 d rest) or with vehicle formulation, as control.

(ii) Test compound plus Chemotherapy Drug Dual Regimen. Mice are treated with the dual regimens, in comparison to the respective monotherapy regimens (individual drugs used at some dosages, within the same experiment). In the dual regimens, test compound (po; 50 mg/kg/d; b.i.d.) is tested in combination with: (a) Dexamethasone (ip, 15 mg/kg, Mon-Fri, for 2 wks); (b) Vincristine (ip, 0.5 mg/kg, every 4 days for 3 wks); (c) Doxorubicin (ip; 1 mg/kg/d, every 4 days for 3 wks); Methotrexate (ip; 5 mg/kg, Mon-Fri on wk1 and wk3 of therapy). Such drugs/doses have been previously validated in xenograft models of pediatric ALL. The more effective regimen or regimens are used in the 2nd phase of the study in xenografts of T-ALL patients.

Evaluation of leukemia progression. Animals are monitored for emergence of leukemia (high WBC; presence of human CD45+ cells, T-cell markers CD2/CD7, CD4/CD8. Mice are sacrificed when exhibiting full-blown leukemia or when moribund, or at d60 after therapy completion if no human ALL cells are detectable in PB. Phenotypic analyses of BM cells from femurs (huCD45, CD2, CD4/CD8 Abs; muCD45) are performed, as well as H&E staining and analyses of tibias, spleen, liver, lymph nodes and abnormal masses.

Endpoints: (i) time to remission following therapy; (ii) leukemia-free survival after treatment regimen; (iii) leukemia progression in drug vs. control groups, with overall survival curves; (iv) number of leukemia blasts at terminal stage (BM); (v) level of parenchymal organ infiltration. Direct comparisons of dual vs. monotherapy groups will be performed.

Example

Figure 9A:
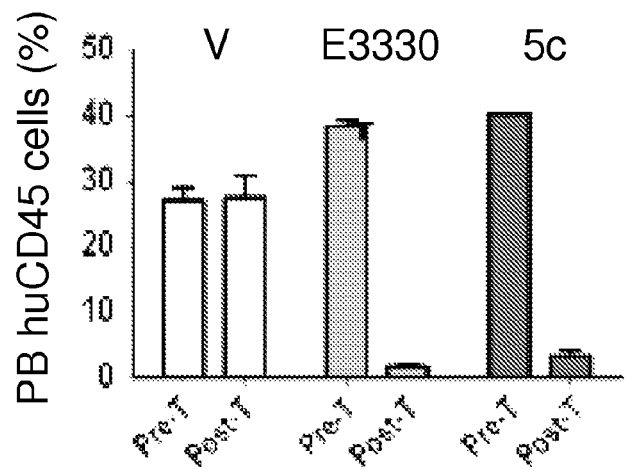
FIG. 9A shows the efficacy of E3330 and Example 5c compared to vehicle control in a xenograft model of leukemia, as determined by the presence of human T-ALL blasts (huCD45+) cells in peripheral blood (PB).
Figure 9B:
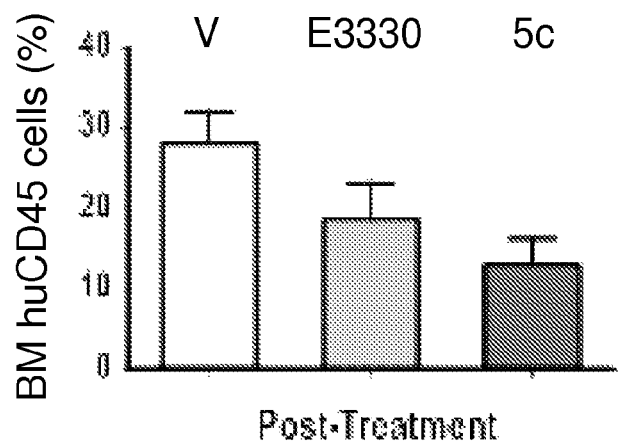
FIG. 9B shows the efficacy of E3330 and Example 5c compared to vehicle control in a xenograft model of leukemia, as determined by the presence of human T-ALL blasts (huCD45+) cells in bone marrow (BM).

E3330 and Example 5c were evaluated in the xenograft model over one cycle of 5 days. NSG mice (n=5/group) transplanted with refractory T-ALL cells. After 14 days post-transplant, the animals were treated with Ref-1 redox inhibitors Example 5c (25 mg/kg/d, b.i.d.) or E3330 (50 mg/kg/d, b.i.d.). At the end of treatment, frequency of human CD45+ cells was performed in the peripheral blood (PB) and in the bone marrow (BM). Animals are sacrificed for analysis. A significant reduction of circulating leukemia blasts after the one cycle of test compound treatment (5 days regimen;) was observed. Analysis at completion of a short treatment regimen (1 cycle) showed that treatment with the Ref-1 redox inhibitors E3330 or 5c resulted in significant reduction of circulating blasts (p<0.05) in comparison to the vehicle group, as well as marked decrease in the frequency of CD45+ in the BM of sacrificed animals, as shown in FIG. 9A and FIG. 9B, respectively.

Example

Ref-1 is expressed by leukemia T-cells in the malignant bone marrow, and its expression is significantly increased in drug-resistant leukemia cells. Immunoblot (IB) demonstrated Ref-1 expression in TAIL7 cells (from relapsed ALL), immortalized T-ALL lines (SupT1, Jurkat, MOLT4), and primary T-ALL cells harvested from patients, including relapse patients. Activation of PI3K is required for interleukin 7-mediated viability, proliferation, glucose use, and growth of T cell acute lymphoblastic leukemia cells. See, J Exp Med 200, 659-669 (2004). An illustrative IL-7-dependent human leukemia T-cell line is described in Blood 103, 1891-1900 (2004).

Example

Western blot analysis. For whole cell lysates, cells are harvested, lysed in RIPA buffer (Santa Cruz Biotechnology; Santa Cruz, Calif.), and protein is quantified and electrophoresed. Nuclear and cytoplasmic extracts are isolated using a conventional method (See, Jackson, (2006)). Immunoblotting is performed using the following antibodies: APE1 (Novus Biologicals; Littleton, Colo.), STAT1, STAT3, STAT5, p-STAT1(Y701), p-STAT3(Y705), p-STAT5 (Y694) (Cell Signaling; Danvers, Mass.), and tubulin (Sigma Aldrich) or GAPDH (Santa Cruz).

Example

Electrophoretic mobility shift assay (EMSA). EMSAs are performed as previously described (Georgiadis, (2008) #15789) with the some modifications. Briefly, for super-shift assay, 6 µg STAT3 antibody (Santa Cruz Biotechnology, Inc, Santa Cruz, Calif.) is pre-incubated with 15 mg nuclear extract from PaCa-2 cells (treated with 50 ng/mL IL-6 for 2 hrs in 2% serum), followed by 1 µg/mL poly(dI-dC).poly(dI-dC) (Amersham Biosciences, Piscataway, N.J.) and 0.1 pmol 5'HEX-labeled double-stranded oligonucleotide DNA (Midland Certified Reagent Company, Midland, Tex.) containing the STAT3 direct repeat consensus sequence for 15 min (Preston, (2005)). For the experiment of APE1 interacting with STAT3, purified APE1 protein is reduced with 2 mM DTT (dithiothreitol) for 10 min and diluted to a final concentration of 4 mg with 0.4 mM DTT in PBS. Reduced APE1 is added to 15 mg nuclear extract as above. The final concentration of DTT in redox reactions is 0.04 mM. For EMSA with treatment with a compound described herein, such as E3330 or Examples 5, the compound is pre-incubated with purified, reduced APE1 in EMSA reaction buffer for 30 min, followed by addition of 3 µg nuclear extract.

Example

Maximum tolerated dose (MTD). The compounds described herein exhibit a wide therapeutic window. Examples E3330, 5a, 5c, and 5e demonstrated good tolerance of oral doses up to 150-200 mg/kg/d, in both single dose and multiple dosing protocols (2 week studies). Single dose MTD for all compounds was greater than 250 mg/kg. and multiple dose MTD was greater than 200 mg/kg. Animals were monitored for up to 14 days after termination of dosing. No significant weight loss was observed. Similar results were observed with intraperitoneal dosing. In each case, doses of 150-200 mg/kg/d are expected to be much higher than those used in treating diseases as described herein.

Example

Biochemistry. The compounds described herein, including E3330, and Examples 5a, 5c, and 5e, do not affect the activation status of other signaling pathways involved in T-ALL. That result is in contrast to what is observed with other compounds such as PI3K/Akt or mTOR. The compounds described herein, including E3330, and Examples 5a, 5c, and 5e, do not affect the phosphorylation state and nuclear translocation of STAT3. Instead, the compounds described herein, including E3330, and Examples 5a, 5c, and 5e, disrupt DNA binding and transcriptional activity of the target TFs of Ref-1, including STAT3, AP-1, and NF-κB).

Compound Examples

Example 1

The following example compounds are described herein and may be prepared as described in the above scheme.

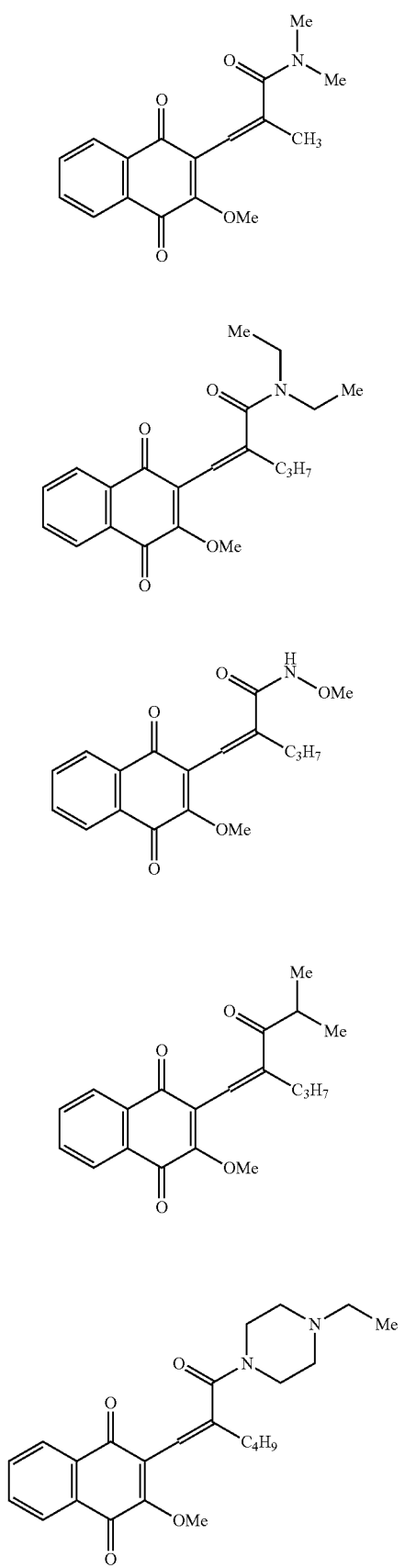
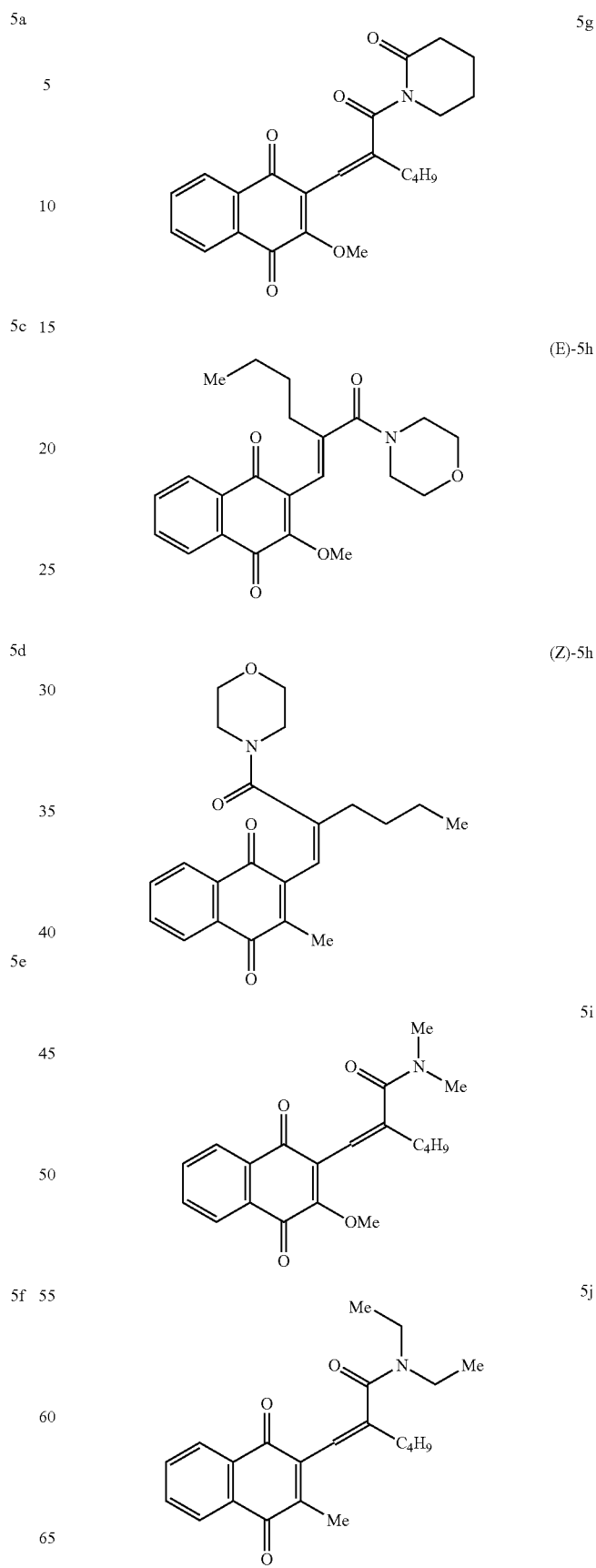

-continued

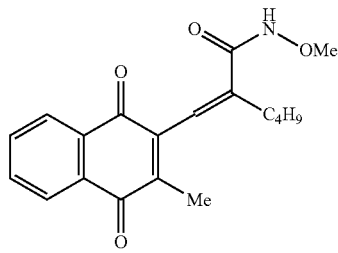

5k

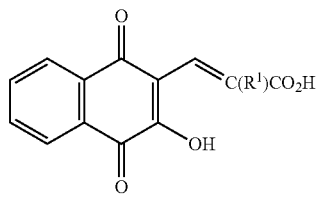

2a: R¹ = Me
2b: R¹ = Pr

Example 2a

In a 2 L 3-necked flask equipped with a mechanical stirrer and a gas dispersion fritted tube was place 2-iodo-3-hydroxy-1,4 naphthoquinone (18 g, 0.06 mol) and methacrylic acid (12.9 g, 0.15 mol) in a solution of potassium carbonate (41.4 g, 0.3 mol) in water (600 mL). The reaction mixture was stirred and sparged with argon for 30 min. Palladium(II) acetate (0.67 g, 0.003 mol) was added and sparging continued for an additional 30 min. The resulting mixture was heated in an oil-bath at 100° C. HPLC analysis showed the reaction was complete after 1 hr. The reaction mixture was cooled to room temperature and the black Pd metal was filtered. The filtrate was placed in a 2 L 3-necked flask equipped with a mechanical stirrer, cooled in an ice-methanol bath and acidified with 50% H3PO4 (160 mL) to pH=2. After stirring for 1 hr, the solid was collected, washed with water (1 L), a mixture of 20% acetone in water (500 mL) and air dried to give 12.6 g (81%) of 2a as a mustard colored solid. HPLC analysis showed a purity of 98%. NMR (d4-MeOH: d6-DMSO; 1:2) δ 7.6-8.2 (m, 4H), 7.3 (q, 1H), 4.7 (br s, 2H), 1.8 (d, 3H).

Example 2b

Similarly, 2b was prepared in 72% yield. NMR (d6-DMSO) δ 12.6 (br s, 1H), 11.65 (br s, 1H), 8.0 (m, 2H), 7.8 (m, 2H), 7.15 (s, 1H), 2.1 (m, 2H), 1.4 (m, 2H), 0.8 (m, 3H).

3a: R¹ = Me
3b: R¹ = Pr

Example 3a

To a suspension of 2a (3.61 g, 0.014 mol) and DMF (0.1 mL) in dichloromethane (75 mL) was added oxalyl chloride (17.5 mL of 2M in CH2Cl2, 0.035 mol) over 20 min at room temperature. The resulting mixture was stirred at room temperature over night and then was concentrated under reduced pressure to give 4.1 g (100%) 3a as a brown solid. This solid was used directly in the next step. NMR (CDCl3) δ 7.8-8.2 (m, 2H), 7.7-7.8 (m, 2H), 7.65 (q, 1H), 1.9 (d, 3H).

Example 3b

Similarly, 3b was prepared. NMR (CDCl3) δ 7.8-8.2 (m, 2H), 7.7-7.8 (m, 2H), 7.4 (s, 1H), 2.1-2.4 (m, 2H), 1.2-1.7 (m, 2H), 0.6-1.0 (m, 3H).

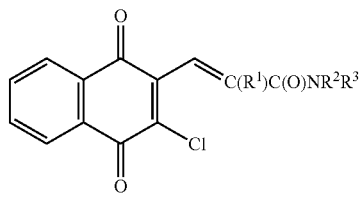

4a: $R^1$ = Me, $R^2$ = $R^3$ = Me
4b: $R^1$ = Me, $R^2$ = H, $R^3$ = Me
4c: $R^1$ = Pr, $R^2$ = $R^3$ = Et
4d: $R^2$ = Pr, $R^2$ = H, $R^3$ = OMe
4e: $R^1$ = Pr, $R^2$ = $R^3$ = Me

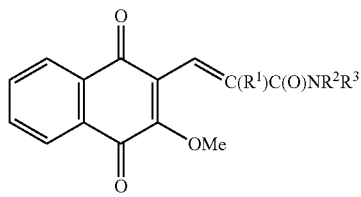

5a: $R^1$ = Me, $R^2$ = $R^3$ = Me
5b: $R^1$ = Me, $R^2$ = H, $R^3$ = Me
5c: $R^1$ = Pr, $R^2$ = $R^3$ = Et
5d: $R^2$ = Pr, $R^2$ = H, $R^3$ = OMe
5e: $R^1$ = Pr, $R^2$ = $R^3$ = Me

Example 4a

To a solution of crude 3a (8.85 g, 0.03 mol) in dichloromethane (50 mL) was a solution of dimethyl amine hydrochloride (3.67 g, 0.945 mol) and diisopropyl amine (11.6 g, 0.09 mol) in dichloromethane (50 mL) at room temperature over 45 min. HPLC analysis after 15 min showed the reaction was complete. The reaction mixture was washed with water (100 mL), 1M HCl (2×100 mL), brine (100 mL), filtered through 1PS filter paper and concentrated under reduced pressure to give 8.8 g of a deep red solid. The solid was flash chromatographed over silica gel (150 g) with anhydrous sodium sulfate (20 g) on top packed with hexane. The column was eluted with 125 mL portions of 15% ethyl acetate in hexane for fractions 1-4, 25% ethyl acetate in hexane for fractions 5-8, 35% ethyl acetate in hexane for fractions 9-16, and 50% ethyl acetate in hexane for fractions 17-32. All fractions were checked by TLC (ethyl acetate: hexane; 1:1) and some fractions by HPLC. The product was eluted in fractions 21 to 30. They were combined and concentrated under reduced pressure to give 6.5 g of an orange solid. This solid was suspended over 15% ethyl acetate in hexane (50 mL) and stirred for 15 min. The solid was collected and air dried to give 6.1 g (67%) of 4a as an orange solid. HPLC analysis showed a purity of 99%. NMR (CDCl3) δ 7.9-8.2 (m, 2H), 7.5-7.8 (2H), 6.5 (q, 1H), 3.1 (br s, 6H), 1.9 (d, 3H).

Example 4b

Similarly, 4b (67%) was prepared. NMR (CDCl3) δ 7.9-8.2 (m, 2H), 7.6-7.8 (m, 2H), 6.9 (q, 1H), 6.3 (br s, 1H), 2.9 (d, 3H), 1.9 (d, 3H).

Example 4c

Similarly, 4c (62%) was prepared. NMR (CDCl3) δ 8.1-8.3 (m, 2H), 7.7-7.8 (m, 2H), 6.1 (s, 1H), 3.6 (br d, 4H), 2.2 (t, 2H), 1.45 (m, 2H), 1.25 (br s, (6H), 0.9 (t, 3H).

Example 4d

Similarly, 4d (73%) was prepared. NMR (CDCl3) δ 8.85 (s, 1H), 8.25 (m, 2H), 8.1 (m, 2H), 6.65 (br s, 1H), 3.9 (s, 3H), 2.2 (t, 2H), 1.5 (m, 2H), 0.85 (t, 3H).

Example 4e

Similarly, 4e (59%) was prepared. NMR (CDCl3) δ 7.9-8.2 (m, 2H), 7.6-7.8 (m, 2H), 6.1 (s, 1H), 3.2 (br d, 2H), 2.3-(t, 2H), 1.2-1.7 (m, 2H), 0.9 (t, 3H).

Example 5a

To a solution of 4a (4.25 g, 0.014 mol) in methanol (100 mL) was added a solution of sodium methoxide in methanol (4.2 mL of 5M) in one portion under argon. The reaction mixture was acidified to pH=3 by using 3M HCl (3.5 mL), and then was concentrated under reduced pressure. The resulting residue was dissolved in ethyl acetate (150 mL), washed with water (2×75 m), brine (1×100 mL), filtered through 1PS filter paper and concentrated under reduced pressure to give 4.2 g an oil which solidified. This solid was triturated with hexane (50 mL) for 30 min and the solid was collected and air dried to give 3.8 g (86%) of 5a (86%) as a light orange solid. HPLC analysis showed a purity of 100%. NMR (CDCl3) δ 8.1 (m, 2H), 7.8 (m, 2H), 6.3 (s, 1H), 4.15 (s, 3H), 3.2 (br d, 6H), 1.8 (s, 3H).

Example 5c

Similarly, 5c (96%) was prepared. HPLC analysis showed a purity of 99%. NMR (CDCl3) δ 8.15 (m, 2H), 7.75 (m, 2H), 6.2 (s, 1H), 4.1 (s, 3H), 3.6 (br d, 4H), 2.2 (t, 2H), 1.4 (m, 4H), 1.25 (br d, 4H), 0.85 (t, 3H).

Example 5d

Similarly, 5d (83%) was prepared. HPLC analysis showed a purity of 99%. NMR (CDCl3) δ 8.1 (m, 2H), 7.75 (m, 2H), 6.65 (s, 1H), 4.15 (s, 3H), 3.9 (3H), 2.2 (t, 2H), 1.45 (m, 2H), 0.85 (t, 3H).

Example 5e

Similarly, 5e was prepared. HPLC analysis showed a purity of 100%. NMR (CDCl3) δ 8.15 (m, 2H), 7.8 (m, 2H), 6.2 (s, 1H), 4.15 (s, 3H), 3.2 (br d, 6H), 2.2 (t, 2H), 1.45 (m, 2H), 0.9 (t, 3H).

Comparative Example 5b

Similarly, 5b (94%) was prepared. HPLC analysis showed a purity better than 93%. NMR (CDCl3) δ 8.1 (m, 2H), 7.75 (m, 2H), 7 (s, 1H), 6.1 (br s, 1H), 4.1 (s, 3H), 2.95 (d, 3H), 1.85 (s, 3H).

In each of the foregoing examples, as well as throughout the description herein, it is to be understood that the geometry of the double bond may be (E), (Z), or any mixture thereof, unless indicated otherwise. For example, (Z)-5 h corresponds to the (Z) isomer, and (E)-5 h corresponds to the (E) isomer of the double bond.

What is claimed is:

1. A method for treating leukemia selected from the group consisting of childhood acute lymphoblastic leukemia (ALL), infant ALL, T-cell ALL (T-ALL), relapsed ALL, refractory ALL, and glucocorticoid-resistant ALL in a patient, the method comprising the step of administering an effective amount of at least one compound selected from the group consisting of

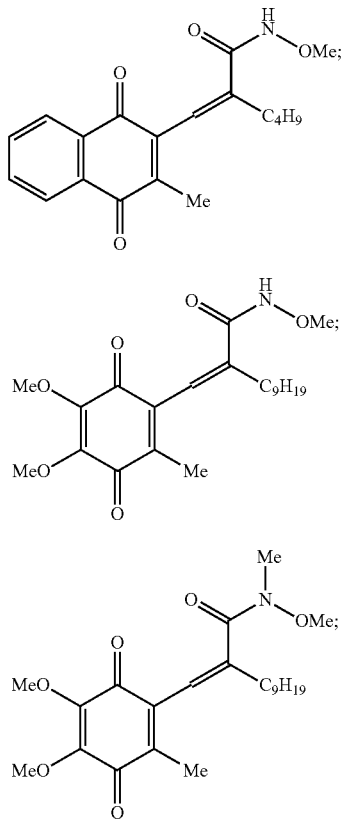

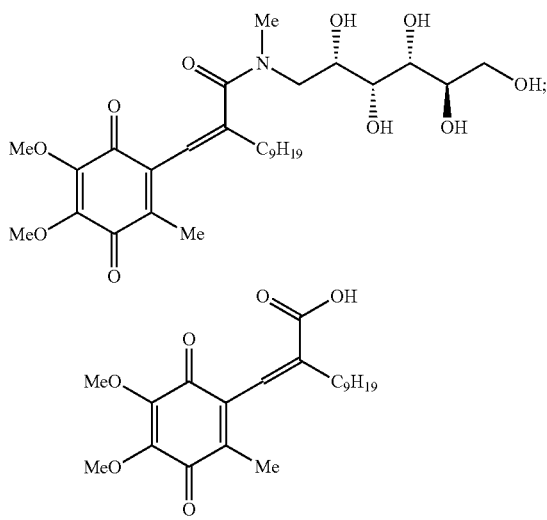

-(5-(2,3-dimethoxy-6-methyl 1,4-benzoquinoyl)]-2-nonyl-2-propenoic acid (E3330)) or a pharmaceutically acceptable salt or solvate thereof.

2. The method of claim 1 wherein the compound is a selective inhibitor of the Ref-1 redox function.

3. The method of claim 1 further comprising administering one or more antileukemia chemotherapeutic agent or one or more antileukemia enzyme inhibitor, or a combination thereof.

4. The method of claim 3 wherein the one or more antileukemia chemotherapeutic agent is selected from the group consisting of dexamethasone, vincristine, doxorubicin, and methotrexate.

5. The method of claim 1 further comprising administering one or more carriers, diluents, or excipients, or a combination thereof.

* * * * *